United States Patent
Cohen et al.

(10) Patent No.: US 6,893,611 B1
(45) Date of Patent: May 17, 2005

(54) AUTOMATIC DEVICE FOR DISPENSING SAMPLES IN LIQUID MEDIUM FOR USE IN CHEMICAL OR BIOLOGICAL REACTIONS

(75) Inventors: Patrick Cohen, Deuil la Barre (FR); Gilles Thomas, Paris (FR); Jean-Marc Victor, Paris (FR)

(73) Assignee: Fondation Jean Dausset-Ceph, Paris (FR)

( * ) Notice: Subject to any disclaimer, the term of this patent is extended or adjusted under 35 U.S.C. 154(b) by 0 days.

(21) Appl. No.: 09/646,668

(22) PCT Filed: Mar. 19, 1999

(86) PCT No.: PCT/FR99/00640

§ 371 (c)(1),
(2), (4) Date: Sep. 20, 2000

(87) PCT Pub. No.: WO99/49320

PCT Pub. Date: Sep. 30, 1999

(30) Foreign Application Priority Data

Mar. 20, 1998 (FR) .............................. 98 03446

(51) Int. Cl.[7] .............................................. G01N 35/00
(52) U.S. Cl. ............................ 422/63; 422/67; 422/100
(58) Field of Search ............................ 422/100, 62–67; 436/180, 43; 141/237; 73/863.32, 864, 864.01, 864.11, 864.24, 864.25; 435/287.3

(56) References Cited

U.S. PATENT DOCUMENTS

| | | | | |
|---|---|---|---|---|
| 3,886,253 A | * | 5/1975 | Friendship | 264/238 |
| 4,228,864 A | * | 10/1980 | Berger et al. | 177/145 |
| 5,096,670 A | * | 3/1992 | Harris et al. | 422/65 |
| 5,141,871 A | * | 8/1992 | Kureshy et al. | 436/47 |
| 5,270,210 A | * | 12/1993 | Weyrauch et al. | 436/43 |
| 5,338,688 A | | 8/1994 | Deeg et al. | 436/180 |
| 5,674,006 A | * | 10/1997 | Islam et al. | 366/239 |
| 5,788,928 A | * | 8/1998 | Carey et al. | 422/102 |
| 5,807,522 A | * | 9/1998 | Brown et al. | 422/50 |
| 5,927,547 A | | 7/1999 | Papen et al. | |
| 6,079,283 A | | 6/2000 | Papen et al. | |
| 6,083,762 A | | 7/2000 | Papen et al. | |
| 6,083,763 A | * | 7/2000 | Balch | 436/518 |
| 6,094,966 A | | 8/2000 | Papen et al. | |
| 6,112,605 A | | 9/2000 | Papen et al. | |
| 6,148,878 A | * | 11/2000 | Ganz et al. | 141/129 |
| 6,159,368 A | * | 12/2000 | Moring et al. | 210/321.75 |

FOREIGN PATENT DOCUMENTS

| | | |
|---|---|---|
| EP | 438 136 | 7/1991 |
| EP | 810 438 | 12/1997 |
| WO | 97/26539 | 7/1997 |
| WO | 97/44134 | 11/1997 |
| WO | WO 98/45205 | 10/1998 |

* cited by examiner

*Primary Examiner*—Jill Warden
(74) *Attorney, Agent, or Firm*—Foley & Lardner LLP (57) ABSTRACT

An automatic device for dispensing samples in liquid medium for use in chemical or biological reactions, including a first supply plate with N receptacles, a second supply plate with M receptacles, a removable plate for sample and a piezoelectric micropipette.

20 Claims, 2 Drawing Sheets

AUTOMATIC DEVICE FOR DISPENSING SAMPLES IN LIQUID MEDIUM FOR USE IN CHEMICAL OR BIOLOGICAL REACTIONS

The present invention relates to an automatic device for producing a plurality of reaction samples from several constituents for implementing chemical or biological reactions in liquid medium, in particular the dosing of at least one particular constituent in a biological specimen.

Numerous methods have been developed for identifying, detecting or quantifying analytes in chemical or biological constituents.

These methods are usually based on the formation of complexes by affinity reaction between members of a specific binding pair.

Reactions, of ligand/receptor type, result for example from interactions between an antigen and a specific antibody, from hybridization between two complementary nucleic acid sequences or from a phenomenon of recognition between the binding site of a protein, for example an enzyme, hormone, or other biological entity, and its ligand, substrate or receptor.

The formation of an affinity complex makes it possible to reveal the presence of the sough-after analyte in the sample. This analyte may possibly be quantified, if it is possible to separate the complexed forms from those remaining in the free state, or to measure the degree of occupancy of the specific ligands of the analyte.

This type of method for detecting and quantifying an analyte present in a constituent, sometimes in trace quantities, offers great benefit for research or analysis laboratories, in particular laboratories for clinical or biological analysis.

However, for routine use, the methods must be able to be applied simultaneously to a large number of constituents. Furthermore, for one and the same constituent, it is often necessary to carry out several tests so as to reveal the formation of various complexes, to dose several analytes of this constituent.

Moreover, in the field of genetic analysis, the technique of genetic amplification dubbed "Polymerase Chain Reaction" (PCR) makes it possible in particular, on the basis of DNA specimens, to identify DNA marker sequences for genetic diseases, to identify and isolate DNA sequences with a view to cloning or else to quantitatively dose particular DNA sequences.

This technique makes it possible to amplify in a sample a particular DNA sequence with a view to analyzing it.

The reaction samples employed in this PCR technique consist of three different constituents: the biological specimen containing the DNA, the specific primers (oligonucleotides) for the sequence to be analyzed and the PCR mix comprising the polymerase and the nucleotides.

The implementation of such a technique on a large number of different DNA specimens, then requires the implementation of a large number of reaction samples produced by cross-combining at least two series of numerous constituents.

More generally, the characterization of a large number of chemical or biological properties over a wide selection of different constituents requires the production of a large number of samples from at least two series of numerous different constituents.

In order to lower the costs of implementing such characterization techniques, it is currently advisable to reduce the volume of the constituents used as far as possible.

In particular, in the field of genetic analysis, the current trend is to reduce the volumes of constituents handled by a factor of 1000, thereby taking them from a few microliters to a few nanoliters.

Thus, currently, the technology of DNA microchips is being developed, making it possible to carry out simultaneous reactions of a large number of reagents with one and the same biological specimen on a miniaturized sample support.

However, such a technology does not make it possible to produce a large number of reaction samples automatically from at least two series of different constituents.

As compared with the state of the art, the present invention proposes a novel automatic device making it possible to carry out the controlled dispensing of nanovolumes of liquid constituents into a plate containing a large number of miniaturized cavities so as to perform multiple mixings in nanovolumes in order to produce reaction samples.

More particularly, according to the invention, there is provided an automatic device for producing a plurality of reaction samples from several constituents for implementing chemical or biological reactions in liquid medium, in particular the dosing of at least one particular constituent or analyte in a biological specimen, such a device comprising:

a first supply plate, in particular a removable plate of the microplate type, comprising N receptacles each intended to contain a constituent, a second supply plate, in particular a removable plate of the microplate type, comprising M receptacles each intended to contain a constituent, a removable plate for samples, comprising a plurality of cavities arranged in the form of an array comprising at least N rows and at least M columns, each cavity exhibiting a volume of the order of a few tens of nanoliters, and being intended to contain a mixture of constituents originating from the first and second supply plates, a piezoelectric micropipette able to sample a determined amount of constituent and to deliver drops of volume of the order of a nanoliter, means for displacing the piezoelectric micropipette along at least two perpendicular axes Y, Z so that it can sample from each filled receptacle of the first and second supply plates, the determined amount of a constituent, and means of relative displacement of the piezoelectric micropipette and of the sample plate, which are associated with means for triggering discharge of the micropipette in such a way that the latter delivers at least one drop of constituent into each cavity of the sample plate.

The expressions N receptacles, and M receptacles of the first and second supply plates are understood to mean the receptacles intended to be actually filled with a constituent. It should of course be understood that these first and second supply plates can contain a number of receptacles greater than N respectively M, with a certain number of unused useful receptacles.

Thus, by virtue of the combining of the aforesaid means of the device according to the invention, it is possible to produce thousands of different samples per hour in volumes of a few nanoliters with a view to performing chemical or biological reactions.

By virtue of the miniaturization of the sample volumes, the cost of said chemical or biological reactions is thus reduced.

Apart from the fact that the automation of the device makes it possible to obtain a high rate of production of sample plates, it makes it possible to comply with proper safety and hygiene conditions.

According to other advantageous and nonlimiting characteristics of the device according to the invention:

The relative displacement of the piezoelectric micropipette and of the sample plate is continuous and the discharge triggering means are able to trigger discharges of the micropipette at regular time intervals as a function of the constant speed of relative displacement of said micropipette and of the sample plate, independently of the presence or otherwise of a cavity of the sample plate in line with the micropipette.

The means of relative displacement are means for advancing the sample plate along an axis X parallel to the rows of the arrays of cavities and/or along an axis Y parallel to the columns of the arrays of cavities, the piezoelectric micropipette remaining stationary above the sample plate during the filling of said cavities.

The means of relative displacement are means for advancing the micropipette along axes X and/or Y respectively parallel to the rows and to the columns of the arrays of cavities of the sample plate which remains stationary beneath the micropipette during the filling of said cavities.

The advancing means comprise a stepper or DC motor, and the discharge triggering means comprise a counter of the steps of the motor able to send a discharge triggering signal every $N_1$ steps.

The piezoelectric micropipette is able to count the number of drops which it delivers and to stop discharging after a determined number of drops delivered.

The device comprises a refrigerating tray supporting the sample plate.

There is provided at least one optical system such as the emission/reception of a laser carpet, in line with the sample plate, able to count the number of drops delivered with each discharge of the piezoelectric micropipette, and to transmit this number to a coordination device so that an order for a second pass in line with a cavity or several cavities is sent to the micropipette when a discrepancy is noted between the counted number of drops discharged and the designated theoretical number of drops.

The device comprises another piezoelectric micropipette identical to the first, the two micropipettes operating alternately.

The device comprises an automatic washing station associated with each piezoelectric micropipette ensuring the decontamination of the latter.

Each washing station comprises means for filling the piezoelectric micropipette with a carrier liquid and optical means for verifying the proper filling of said micropipette.

Each piezoelectric micropipette comprises two conducting parts separated by a nonconducting material, which are electrically linked at the upper part to an electrical system, so that when the orifice of the piezoelectric micropipette comes into contact with a constituent of a receptacle of the first or of the second supply plate, it brings about closure of the electrical circuit formed by the two electrically linked conducting parts of said micropipette, which commands the stoppage of the vertical displacement of the micropipette.

The description which follows with regard to the appended drawings, given by way of nonlimiting examples, will clearly elucidate that of which the invention consists and how it may be embodied.

EMBODIMENTS OF THE INVENTION

Figure 1:
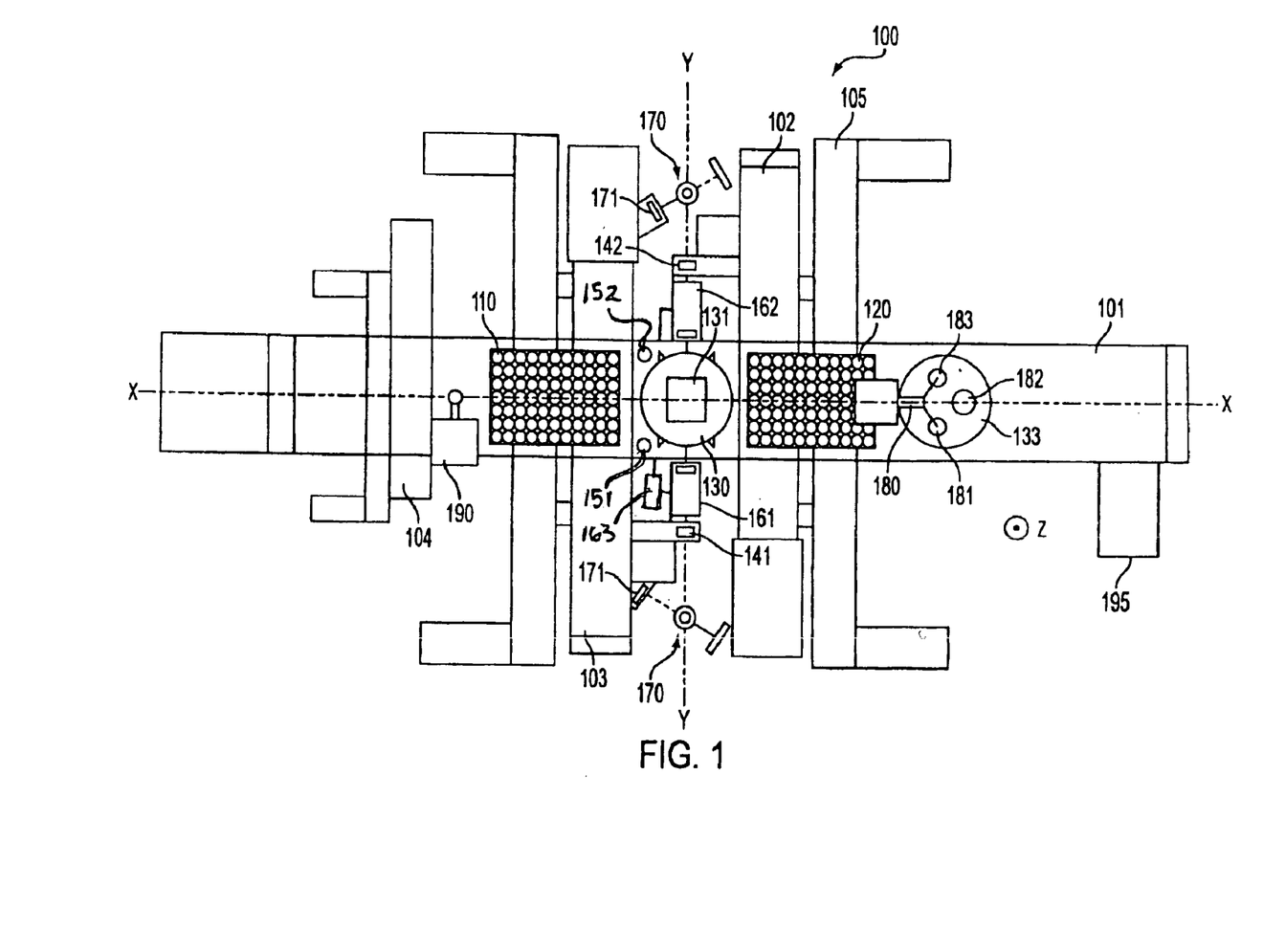
FIG. 1 is a diagrammatic plan view of an embodiment of the automatic device according to the invention.

Represented in FIG. 1 is an automatic device 100 for producing a plurality of samples from several constituents for implementing chemical or biological reactions in liquid medium, here in particular the gene amplification technique (PCR technique).

This device 100 comprises a first supply plate 110, here a removable plate of the microplate type which comprises 96 wells or cavities of a capacity of the order of from 100 to 300 microliters, each intended to contain a constituent, here a DNA specimen.

Advantageously, each receptacle contains a different constituent.

It furthermore comprises a second supply plate 120, here identical to the first plate, that is to say a removable plate of the microplate type comprising 96 wells or cavities, each intended to contain a constituent. In the particular case described, the constituents placed in the cavities of the second supply plate 120 are primers which can be fluorescent, consisting of specific oligonucleotides for the particular DNA sequences to be amplified.

It is also advantageous for each receptacle of the second supply plate 120 to contain a different constituent.

There is provided a removable sample plate 130, which comprises a plurality of cavities 134 (see FIG. 2) arranged in the form of an array 131, here a square arrays which comprises 100 rows and 100 columns for example.

Figure 2:
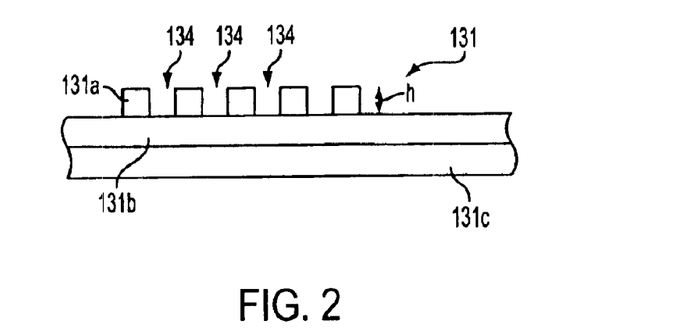
FIG. 2 is a partial cross-sectional view of the sample plate of the automatic device according to the invention.

Each cavity 134 of the sample plate 130 exhibits a volume of the order of a few tens of nanoliters, here of the order of 60 nanoliters, and is intended to contain a mixture of constituents originating from the first and second supply plates 110, 120.

Figure 3:
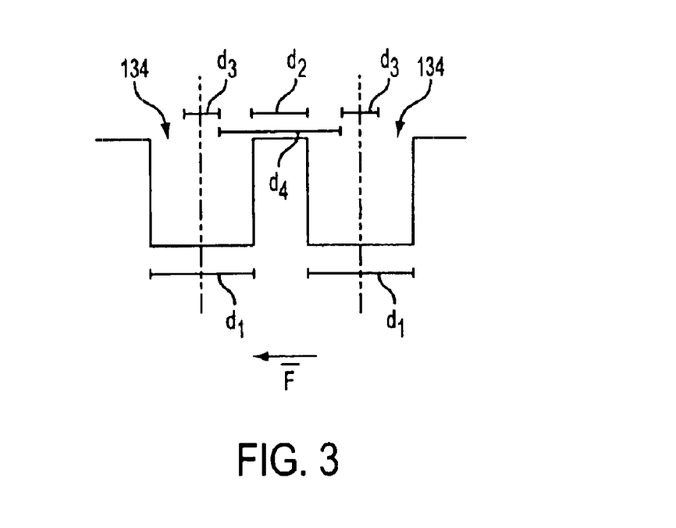
FIG. 3 is a diagrammatic view of a detail of FIG. 2.

More particularly, the arrays 131 of the sample plate 130 here exhibits a length and a width of around 5.5 cm, the cavities 134 are spaced apart successively in a row by a length $d_2$ of the order of 150 µm (see FIG. 3). They exhibit a width $d_1$ of around 400 µm for a depth h (see FIG. 2) of the order of 400–500 µm.

The sample plate 130 consists of a glass support wafer 131b, transparent to UV rays, onto which is chemically bonded ("anodic bonding") a silicon grid 131a whose holes correspond to the cavities 134 of the sample plate. This silicon grid 131a is made from a silicon wafer masked and drilled by photolithography.

The first supply plate 110 and the second supply plate 120 are disposed on either side of the sample plate 130 along an axis X, on a bench 101.

As will be described in greater detail later, this bench 101 is here able to move in translation along the X axis.

It is interesting to note that according to an advantageous characteristic of the device 100, the sample plate 130 is disposed on a refrigerating support 131c, so that the small amount of product which arrives in each of the cavities of the arrays 131 of the sample plate 130 is cooled and possibly frozen.

The evaporation of the product placed in each of the cavities of the sample plate is thus limited.

According to the example represented, there is provided in proximity to the sample plate 130 on the bench 101, two vessels 151, 152 disposed symmetrically on either side of the X axis of the bench 101 and intended to each contain another constituent, here the PCR mix mixture which contains a polymerase and the nucleotides. These vessels 151, 152 are able to contain 100 to 500 microliters of product.

The device 100 comprises a first piezoelectric micropipette 141 able to sample a determined amount of constituent and to deliver drops of constituent of a volume of the order of a nanoliter.

The amount sampled by the piezoelectric micropipette 141 is of the order of a microliter. Of course, provision may be made for it to sample several microliters.

This micropipette 141 is mounted on a motorized rig 103 of the device 100 so as to be able to move along a Y axis transverse to the X axis situated in the same plane as the latter, and along a Z axis perpendicular to the X and Y axes so that it can sample from each filled receptacle of the first and second supply plates 110, 120 the determined amount of a constituent, as will be described later.

Generally, motor means may be provided in the device 100 according to the invention, so as to move the piezoelectric micropipette 141 along the perpendicular X, Y, Z axes.

In the example represented, there is also provided a second piezoelectric micropipette 142 identical to the first piezoelectric micropipette 141 disposed symmetrically with the first relative to the X axis so that the orifices of the micropipettes are perfectly aligned on one and the same Y axis.

The second piezoelectric micropipette 142 is mounted on a motorized rig 102 in such a way as to be able to move along the perpendicular Y and Z axes. Here again, provision may be made for it to be movable along the X axis in a variant embodiment (not represented).

The two piezoelectric micropipettes 141, 142 are able to operate alternately so as to fill the cavities disposed in rows and columns of the arrays 131 of the sample plate 130.

There are provided means of relative displacement of each piezoelectric micropipette 141, 142 and of the sample plate 130, which are associated with means for triggering discharge of each micropipette 141, 142 in such a way that the latter delivers at least one drop of constituent into each cavity 134 of the sample plate 130.

Here, advantageously, the relative displacement of the piezoelectric micropipette 141, 142 and of the sample plate 130 is continuous and the discharge triggering means are able to trigger discharges of the corresponding piezoelectric micropipette 141, 142 at regular time intervals as a function of the constant speed of relative displacement of the micropipette 141, 142 and of the sample plate 130, independently of the presence or otherwise of a cavity 134 of the sample plate 130 in line with the micropipette 141, 142.

To do this, there is provision in order to fill the row-wise cavities of the arrays 131 of the sample plate 130, according to the embodiment represented in FIG. 1, for the means of relative displacement to comprise means for advancing the sample plate 130 along the X axis parallel to the rows of the arrays 131 of cavities 134, the corresponding piezoelectric micropipette 141, 142 remaining stationary above the sample plate 130 during the filling of the cavities of the plate.

Said advancing means comprise a stepper or DC motor 195, and the discharge triggering means comprise a counter of steps of the motor able to send an external electrical discharge triggering signal every $N_1$ steps.

More particularly, according to the example represented, each piezoelectric micropipette 141, 142 advantageously exhibits an ejection frequency of 1000 hertz thereby enabling it to deliver 10 drops of 1 nanoliter in $10^{-2}$ seconds.

It is interesting to stress that the ejection frequency of the piezoelectric micropipette must not be too high so as to avoid any risk of emptying the latter (by cavitation).

The ejection frequency is then chosen in an optimum manner so that it is high enough while avoiding the risks of emptying the micropipette during action.

In the typical case, it is envisaged that with each pass of the piezoelectric pipette above a cavity, the latter shall deliver 10 drops of constituent of 1 nanoliter into the corresponding cavity 134 of the arrays 131 of the sample plate 130.

To do this, the piezoelectric micropipette 141, 142 discharges 10 drops over a distance $d_1$ of 100 μm in the vicinity of each central axis of each cavity 134, as is represented more particularly in FIG. 3.

The piezoelectric pipette then delivers 10 drops of 1 nanoliter in $10^{-2}$ seconds over a distance of 100 μm in the vicinity of each center of each cavity 134 of the arrays 131 of the supply plate, thereby making it possible to determine the continuous speed of advance of 10 mm/s of the arrays 131 of the sample plate with respect to the stationary piezoelectric pipette.

Advantageously, each piezoelectric micropipette 141, 142 is such that it is able to count the number of drops which it delivers and to stop after a determined number of drops, fixed beforehand.

In the present case, it thus stops after 10 drops of constituent delivered.

A stepper or DC motor 195 makes it possible for the bench 101 on which the sample plate sits to be moved continuously, for example along the arrow F as represented in FIG. 3 at a constant speed of 10 mm/s. This motor counts its steps and after a certain number of steps $N_1$ corresponding to the distance traveled $d_1+d_2$, it sends an order (via an external electrical signal) to the relevant piezoelectric micropipette 141, 142, triggering discharge of the 10 drops of constituent, while this pipette is in principle in proximity to a center of a cavity 134. The discharging of the micropipette proceeds over a distance $d_1$ equal to 100 μm after which the micropipette which has in principle counted 10 drops of constituent, stops delivering the constituent of the product.

The stepper or DC motor 195 which continues to count its steps, advances the sample plate by a distance $d_1$ equal to around 500 μm before sending a new discharge triggering order to the piezoelectric micropipette, the latter normally being located in proximity to the center of the next cavity 134 in the same row, and so on and so forth.

It should be noted that these discharge triggering means are independent of the fact that a cavity of the sample plate is located in line with the orifice of the piezoelectric micropipette, but are dependent on the speed of relative advance of the sample plate and of the micropipette, so that when the micropipette triggers a discharge its orifice is located in proximity to a center of a cavity.

Of course, according to a variant (not represented), means for displacing the micropipette relative to the sample plate, the latter remaining stationary, may be provided so as to fill the row-wise cavities of the sample array.

These means for displacing the micropipette can be a stepper or DC motor 195 which counts its steps and which triggers the discharging of the micropipette when the end of the latter passes in the vicinity of a center of a cavity of the sample plate, as described earlier.

Such a means for displacing the micropipette along the Y axis parallel to the columns of the array of the sample plate is used according to the example described to till the cavities of the array column-wise.

On either side of the sample plate 130 disposed on the bench 101, the device 100 comprises means for controlling the number of drops delivered into each cavity, here a system for emitting/receiving a laser carpet 161, 162 whose beam is aligned on the axis of displacement of the micropipettes.

The system for emitting/receiving the laser carpet 161, 162 is able to count up and transmit the number of drops delivered into each cavity by the piezoelectric micropipette, to a coordination device 163, a comparison between the number delivered and the designated theoretical number (here the number 10) is performed by the coordination device and when a discrepancy is noted between the number actually delivered and the designated theoretical number, the coordination device 163 sends an order for a second pass of the piezoelectric micropipette over the relevant cavity or cavities so as to deliver the missing drop or drops. If the discrepancy noted is greater than a given threshold, the system is able to record this discrepancy in a computer file.

As shown in FIG. 1, an automatic washing station 170 is provided in the device 100 for each piezoelectric micropipette 141, 142. Each micropipette having its own washing station as close as possible to the relevant pipette. These two washing stations 170 are disposed symmetrically with respect to the X axis on either side of the bench 101 and are aligned on the axis of displacement of the micropipettes.

Each automatic washing station 170 is such that it makes it possible between each filled row or column of the array, to wash the micropipette with Javel water for example, so as to decontaminate it, and to fill it with a water-immiscible carrier liquid, octane for example. Advantageously, there is provided at each washing station 170, an optical means, such as a laser beam 171 which makes it possible to control the proper filling of the micropipette with the carrier liquid.

Furthermore, the device 100 comprises an automatic system for removing and fitting covers 180 which is fixed on a motorized rig 105 above the bench 101, outside the second supply plate 120 (with respect to the sample plate). This system 180 for removing and fitting covers here comprises three suckers 181, 182, 183 disposed at the end of arms extending radially from a central point, and is able to move along the Z axis so as to seize a cover for example a cover 133 of the sample plate, which cover is made of a glass which is transparent to UV rays, and when the sample plate 130 is placed beneath said system 180, to fit this cover 133 on the filled sample plate 130 so as to close it. The system 180 for removing and fitting covers is also intended for taking off the covers (not represented) of the first and second supply plates before initiating the procedure for filling the array of the sample plate.

Opposite the automatic system 180 for removing and fitting covers, there is provided an automatic system 190 for fitting a seal to the sample plate 130 before setting the cover in place. This system 190 is mounted on a rig 104 above the bench 101 and is motorized in such a way as to move along the Z and Y axes so that, when the sample plate 130 is situated beneath this system 190, by advancing along the X axis, the displacement along the Y axis of the seal fitting system 190 makes it possible to place a circular seal on the sample plate 130. In the case where the latitude of displacement of the bench 101 is limited along the X axis, there may be provided at the level of the automatic seal fitting system 190, another cover removal and fitting system identical to that described earlier and intended for taking off and replacing the cover of the supply plate 110 situated in proximity thereto.

Figure 4:
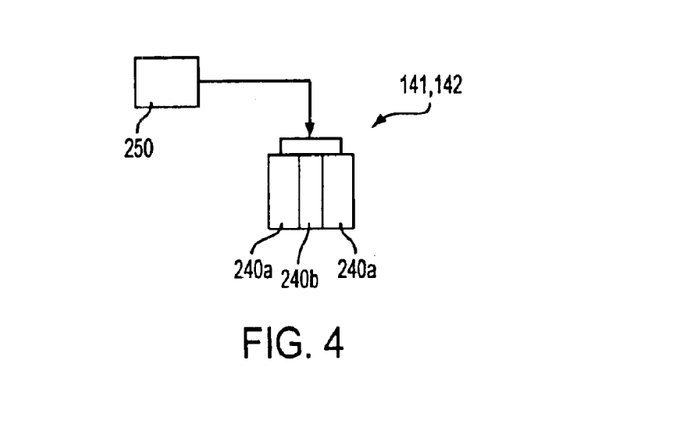

According to a particularly advantageous characteristic, each piezoelectric pipette 141, 142 of the device according to the invention comprises two conducting parts 240a separated by a nonconducting material 240b, which are linked to an electrical system 250, as shown in FIG. 4, so that when the orifice of the micropipette comes into contact with a constituent of a receptacle of the first or the second supply plate, it brings about closure of the electrical circuit, which causes the former to stop in the vicinity of the surface of the liquid.

The micropipette thus comprises a level detector system so that it does not sink too far into each receptacle of each supply plate.

The manner of operation of the device 100 represented in FIG. 1 is as follows.

Firstly, the bench 101 moves along the X axis so as to bring the supply plate 110 beneath a cover removal and fitting system 180, so that the latter takes the cover off this plate, which remains suspended by the suckers above the bench.

Starting from the rest position represented in FIG. 1 in which it is assumed that each of the micropipettes 141, 142 is filled correctly with a carrier liquid, the first micropipette 141 moves along the Y axis so as to come above the bench 101 and the first supply plate 110 moves along the X axis over the bench 101 so that the orifice of the micropipette is located in line with the first receptacle for example.

The first micropipette descends along the Z axis so as to sample a dose of around 1 microliter of the constituent in the receptacle, then rises back into position just above the supply plate 110. The proper priming of the micropipette is then verified by redispensing a few drops of the constituent into the receptacle.

The sample plate 130 then comes into position beneath the micropipette so that its orifice is placed in line with the first cavity of the first row of the array 131 of the sample plate 130.

The stepper or DC motor 195 then displaces the bench 101 so as to continuously advance the array 131 of the sample plate along the X axis at the speed of 10 mm/s (as described earlier) the micropipette discharging at regular time intervals 10 drops of 1 nanoliter at a frequency of 1000 hertz, into each of the cavities of the first row of the array 131 of the sample plate 130.

With each discharge of the micropipette, the system for emitting/receiving the laser carpet 161, 162 counts the drops delivered.

When the micropipette 141 reaches the end of the row, the sample plate 130 changes direction of travel so that the cavities of the array 131 which are already filled pass beneath the micropipette again so that the latter can optionally deliver additional drops into certain cavities which comprise fewer than 10 drops, the correction order having been obtained by virtue of the system for emitting/receiving the laser carpet 161, 162 as described earlier.

The micropipette 141 having performed a second pass then returns by moving along the Y axis to the level of the automatic washing station 170 situated alongside it, so as to be washed with the Javel water (for example) and refilled with the carrier liquid. It then positions itself on standby.

The second micropipette 142 comes into action when the first micropipette 141 has terminated its second pass above the first row of the sample plate 130.

The micropipette 142 performs its translational motion along the Y axis while the first supply plate 110 is moving along the X axis so that the micropipette 142 comes into position in line with the second cavity of the first supply plate 110. It then moves along the Z axis so as to sample a determined amount of the order of 1 microliter of the constituent located in this cavity.

When the second micropipette 142 is filled with the second constituent, it rises slightly along the Z axis so as to verify the priming thereof. It also moves along the Y axis while the bench 101 is bringing the sample plate 130 along the X axis until it is beneath the micropipette 142, so that its orifice is placed in line with the first cavity of the second row of the array 131. The latter advances under the action of the motor, as described earlier, and the micropipette 142 discharges, at regular time intervals, 10 drops at a frequency of 1000 hertz into each of the cavities of the second row of the array 131 of the sample plate 130 when the orifice of the micropipette passes in the vicinity of the center of each of the cavities.

In the same way, having reached the end of the row, the sample plate 130 changes direction of travel and the array passes beneath the micropipette 142 again so that it can perform corrections of discharge into certain cavities, the order having been obtained by virtue of the system for emitting/receiving the laser carpet 161, 162.

And so on, alternately the micropipettes 141, 142 fill the row-wise cavities of the array 131 of the sample plate 130 with the various constituents contained in the receptacles of the first supply plate 110.

Between each sample plate dispensing cycle, the micropipettes are washed in their washing station 170 and are filled with the carrier liquid, their priming having been controlled by virtue of the corresponding laser beam device associated with each of the washing stations 170.

The bench 101 moves along the X axis so that the cover removal and fitting system 180 refits the cover onto the supply plate 110 and takes the cover off the second supply plate 120.

Then comes the column-wise filling of the cavities 134 of the array 131 of the sample plate 130, with the constituents contained in the receptacles of the second supply plate 120 of the device 100.

The micropipettes 141, 142 also operate alternately every other column. Only the filling of a column of the array of the sample plate will thus be described hereinafter.

The micropipette 141 filled with the appropriate carrier liquid moves along the Y axis so as to be placed above the bench 101 while the second supply plate 120 moves along the X axis until it comes beneath the orifice of the micropipette so that the latter can sample an amount of around 1 microliter of the constituent of the first receptacle of the second supply plate. Priming is verified as described earlier.

The micropipette 141 then moves along the Y axis while the bench 101 moves along the X axis so that the orifice of the micropipette is located above the first cavity of the first column of the array 131 of the sample plate 130.

The micropipette 141 then moves at constant speed of around 10 mm/s along the Y axis along the first column of the array, the motion of the translation of the micropipette being provided by a stepper or DC motor.

The micropipette 141 discharges, at regular time intervals, 10 drops at a frequency of 1000 hertz when its orifice passes in the vicinity of the center of each of the cavities of the first column of the array.

With each discharge, the system for emitting/receiving the laser carpet 161, 162 controls the number of drops delivered into the corresponding cavity.

Having reached the end of the column, the micropipette changes direction of travel and passes back above the cavities it has just filled so as to perform any corrections for which the order has been obtained by virtue of the system for emitting/receiving the laser carpet 161, 162.

Next, the micropipette 141 returns to the washing station by moving along the Y axis so as to be washed and refilled with the carrier liquid before positioning itself on standby.

The second micropipette 142 comes into action when the first micropipette 141 has terminated its second pass. It then fills the cavities of the second column with doses of 10 nanoliters of the constituent contained in the second receptacle of the second supply plate.

Thus, the columns and the rows of the array 131 of the sample plate 130 are filled with the various constituents of the first and second supply plates 110, 120.

The bench 101 moves along the X axis so as to position the second plate 120 beneath the system with suckers 180 so that the latter replace the cover on said plate.

Lastly, comes the filling of the cavities 134 of the array 131 of the sample plate 130 with the PCR mix located in the vessels 151.

To do this, the dispensing method is identical to the filling of the rows of the array, as described earlier, the two micropipettes operating alternately.

Each micropipette 141, 142 coming firstly to the level of the bench 101 so as to sample a dose of the constituent located in the vessel 151, 152, then the array 131 of the sample plate comes beneath the orifice of the micropipette and advances at constant speed and with each pass of the center of a cavity, the micropipette delivers 10 drops of the corresponding constituent into the cavity.

Thus, the sample plate 130 is completely filled with two series of different constituents and a common constituent: a first series of constituents originating from the first supply plate corresponding to a series of DNA specimens, a second series of constituents originating from the second supply plate corresponding to a series of specific primers for particular DNA sequences, and a third common constituent, the PCR mix.

The overall volume of these three constituents in each cavity 134 of the array 131 of the sample plate 130, is of the order of 30 nanoliters.

As we have already explained, it is advantageous for the sample plate 130 to be disposed on th refrigerating system so that the amount of constituent arriving in a cavity of the array is cooled. The problems of the evaporation of the very small amounts dispensed into the cavities is thus limited.

When the sample plate 130 is entirely filled, it moves along the X axis to the level of the seal fitting system 190, which descends along the Z axis to the level of the sample plate and moves along the Y axis while the sample plate 130 moves along the X axis, in such a way as to fit a circular seal onto the sample plate 130 around the array of cavities.

Next, the filled sample plate bearing its peripheral seal moves along the X axis so as to be placed beneath the cover removal and fitting system 180, which previously grabbed a cover 133 of the sample plate 130 using its suckers, and holds this cover above the bench 101.

It then receives the cover 133, made of a glass transparent to UV rays, on the seal which it bears.

The sample plate 130 is then ready to undergo the subsequent treatments so as here to implement the PCR technique.

Of course, the device 100 according to the invention makes it possible to fill the sample plate with all kinds of constituents with a view to implementing other chemical or biological reactions in liquid medium.

The device 100 according to the invention exhibits the following advantages.

It is fully automated and makes it possible in a very short time of close to one hour to fill a sample plate comprising 10,000 cavities so as to produce 10,000 different samples of a volume of a few tens of nanoliters.

This is particularly advantageous in the field of genetic analysis where one seeks to limit the reaction volumes used. The device is also particularly advantageous insofar as it produces N×M reaction samples from only N+M specimens.

The sample plate as described according to the invention is removable and reusable after washing.

The device 100 makes it possible to produce a sample plate very hygienically, thus making it possible to avoid contamination. Such a device also makes it possible to produce reaction samples very safely from dangerous constituents.

Lastly, the device 100 is particularly advantageous insofar as it makes it possible to prepare reaction mixtures in a leaktight plate which may subsequently (after possible storage) be sent to an oven so as to undergo temperature cycles therein (for example for implementing PCR reactions).

Of course, the present invention is in no way limited to the embodiment described and represented, but the person skilled in the art will be able to make any variations thereto in accordance with the spirit thereof.

In particular, there may be provision for the array of the sample plate not to be a square array but an array comprising at least N rows corresponding to the N filled receptacles of the first filled supply plate and at least M columns corresponding to the M filled receptacles of the second supply plate.

The first and second supply plates may be simple test-tube support insofar as one seeks to store a larger amount of product than that which can be stored in the microwells of microplate-type plates.

Provision may be made for the device according to the invention to comprise a number greater than 2 of piezoelectric micropipettes operating alternately in a synchronized manner. Such a device can also comprise a larger number (greater than 2) of supply plates, so as to prepare a sample plate from a larger number of series of constituents.

What is claimed is:

1. An automatic device for producing a plurality of reaction samples in liquid medium, wherein said device comprises:

a first supply plate, comprising N receptacles each intended to contain a first constituent, wherein said plate is a removable microplate;

a second supply plate, comprising M receptacles each intended to contain a second constituent, wherein said plate is a removable microplate;

a removable plate for samples, comprising a plurality of cavities arranged in the form of an array comprising at least N rows and at least M columns, wherein each cavity is configured to hold a volume on the order of at least ten nanoliters, wherein said cavities are intended to contain a mixture of constituents originating from said first and second supply plates;

a piezoelectric micropipette, wherein said micropipette is able to sample a predetermined amount of said first and/or second constituents and to deliver a volume on the order of a nanoliter, wherein said piezoelectric micropipette is capable of delivering at least one drop of said first and/or second constituents into each cavity of said removable plate for samples;

a means for displacing said piezoelectric micropipette along at least two perpendicular axes Y, Z so that said piezoelectric micropipette can sample a predetermined amount of said first and/or second constituents from each filled receptacle of said first and second supply plates; and a means for relatively displacing the piezoelectric micropipette and the removable plate for samples.

2. The device of claim 1, further comprising a stepper or DC motor, wherein said stepper or DC motor is configured to advance said piezoelectric micropipette relative to said removable plate for samples.

3. The device according to claim 1, wherein said piezoelectric micropipette is able to count the number of drops said micropipette delivers and to deliver a predetermined number of drops.

4. The device according to claim 1, further comprising a refrigeration tray supporting said removable plate for samples.

5. The device according to claim 1, further comprising at least one optical system, wherein said optical system is in line with said removable plate for samples, and is configured to count the number of drops delivered with each discharge of said piezoelectric micropipette, and to transmit this number to a coordination device, and wherein the coordination device is configured to send an order for a second pass in line with a cavity or several cavities to the micropipette when a discrepancy is noted between the counted number of drops discharged and the designated theoretical number of drops.

6. The device according to claim 1, further comprising a second piezoelectric micropipette, wherein said second piezoelectric micropipette is identical to said piezoelectric micropipette and both said piezoelectric micropipette and said second piezoelectric micropipette are configured to operate alternately.

7. The device according to claim 1, further comprising an automatic washing station for said piezoelectric micropipette, wherein each washing station is configured to decontaminate said piezoelectric micropipette.

8. The device according to claim 7, wherein said washing station comprises a means for filling said piezoelectric micropipette with a water-immiscible carrier liquid and an optical means for verifying the proper filling of said piezoelectric micropipette.

9. The device according to claim 1, wherein said piezoelectric micropipette comprises two conducting parts separated by a nonconducting material, which are linked at the upper part to an electrical system, so that when the orifice of the piezoelectric micropipette comes into contact with a constituent of a receptacle of the first or of the second supply plate, it brings about closure of the electrical circuit formed by the two electrically linked conducting parts of said piezoelectric micropipette, which commands the stoppage of the vertical displacement of said piezoelectric micropipette.

10. The device according to claim 1, further comprising an automatic means for fitting a seal on said sample plate.

11. The device according to claim 1, further comprising an automatic system configured to remove and fit a cover on said first and second supply plates as well as on a filled sample plate.

12. The device according to claim 1, wherein said first and second supply plates are disposed along the X axis on either side of said removable plate for samples, wherein said plates are configured to be carried together by a movable bench along said X axis.

13. The device according to claim 1, wherein the arrays of said cavities of said removable plate for samples is a square array with N equal to M.

14. The device according to claim 13, wherein said arrays have a width of around 5 cm, and comprise 100 columns and 100 rows with cavities of width ($d_1$) equal to around 400 $\mu$m and of depth equal to around 400–500 $\mu$m, two successive cavities in one row being spaced apart by a distance ($d_2$) equal to around 150 $\mu$m.

15. The device according to claim 1, further comprising vessels, wherein said vessels comprise different constituents disposed in proximity to said removable plate for samples.

16. The device of claim 1, further comprising a stepper or DC motor, wherein said stepper or DC motor is configured to advance said removable plate for samples relative to said piezoelectric micropipette.

17. The device of claim 1, further comprising means for triggering discharge of the micropipette in such a way that the micropipette is able to deliver at least one drop of constituent into each cavity of the sample plate.

18. An automatic device for producing a plurality of reaction samples in liquid medium, wherein said device comprises:
- a first supply plate, comprising N receptacles each intended to contain a first constituent, wherein said plate is a removable microplate;
- a second supply plate, comprising M receptacles each intended to contain a second constituent, wherein said plate is a removable microplate;
- a removable plate for samples, comprising a plurality of cavities arranged in the form of an array comprising at least N rows and at least M columns, wherein each cavity is configured to hold a volume on the order of at least ten nanoliters, wherein said cavities are intended to contain a mixture of constituents originating from said first and second supply plates;
- a piezoelectric micropipette, wherein said micropipette is able to sample a predetermined amount of said first and/or second constituents and to deliver a volume on the order of a nanoliter, wherein said piezoelectric micropipette is capable of delivering at least one drop of said first and/or second constituents into each cavity of said removable plate for samples;
- a means for displacing said piezoelectric micropipette along at least two perpendicular axes Y, Z so that said piezoelectric micropipette can sample a predetermined amount of said first and/or second constituents from each filled receptacle of said first and second supply plates;
- a means for displacing the piezoelectric micropipette relative to the removable plate for samples; and
- a refrigeration tray supporting said removable plate for samples.

19. An automatic device for producing a plurality of reaction samples in liquid medium, wherein said device comprises:
- a first supply plate, comprising N receptacles each intended to contain a first constituent, wherein said plate is a removable microplate;
- a second supply plate, comprising M receptacles each intended to contain a second constituent, wherein said plate is a removable microplate;
- a removable plate for samples, comprising a plurality of cavities arranged in the form of an array comprising at least N rows and at least M columns, wherein each cavity is configured to hold a volume on the order of at least ten nanoliters, wherein said cavities are intended to contain a mixture of constituents originating from said first and second supply plates;
- a piezoelectric micropipette, wherein said micropipette is able to sample a predetermined amount of said first and/or second constituents and to deliver a volume on the order of a nanoliter, wherein said piezoelectric micropipette is capable of delivering at least one drop of said first and/or second constituents into each cavity of said removable plate for samples;
- a means for displacing said piezoelectric micropipette along at least two perpendicular axes Y, Z so that said piezoelectric micropipette can sample a predetermined amount of said first and/or second constituents from each filled receptacle of said first and second supply plates;
- a means for displacing the piezoelectric micropipette relative to the removable plate for samples; and
- at least one optical system, wherein said optical system is in line with said sample plate and is configured to count the number of drops delivered with each discharge of said piezoelectric micropipette, and to transmit this number to a coordination device, and wherein the coordination device is configured to send an order for a second pass in line with a cavity or several cavities to the micropipette when a discrepancy is noted between the counted number of drops discharged and the designated theoretical number of drops.

20. An automatic device for producing a plurality of reaction samples in liquid medium, wherein said device comprises:
- a first supply plate, comprising N receptacles each intended to contain a first constituent, wherein said plate is a removable microplate;
- a second supply plate, comprising M receptacles each intended to contain a second constituent, wherein said plate is a removable microplate;
- a removable plate for samples, comprising a plurality of cavities arranged in the form of an array comprising at least N rows and at least M columns, wherein each cavity is configured to hold a volume on the order of at least ten nanoliters, wherein said cavities are intended to contain a mixture of constituents originating from said first and second supply plates;
- a piezoelectric micropipette, wherein said micropipette is able to sample a predetermined amount of said first and/or second constituents and to deliver a volume on the order of a nanoliter, wherein said piezoelectric micropipette is capable of delivering at least one drop of said first and/or second constituents into each cavity of said removable plate for samples;
- a means for displacing said piezoelectric micropipette along at least two perpendicular axes Y, Z so that said piezoelectric micropipette can sample a predetermined amount of said first and/or second constituents from each filled receptacle of said first and second supply plates; and a means for displacing the piezoelectric micropipette relative to the removable plate for samples; and an automatic washing station for each piezoelectric micropipette, wherein said washing station is configured to decontaminate said piezoelectric micropipette.

* * * * *